United States Patent [19]

Serban et al.

[11] 4,314,065

[45] Feb. 2, 1982

[54] PHENYLAMINE SUBSTITUTED ON AMINE WITH A BENZO(OXA, THIA OR DI) AZOLE GROUP

[75] Inventors: Alexander Serban, Doncaster; Keith G. Watson, Box Hill North, both of Australia; John E. D. Barton, Reading, England

[73] Assignee: ICI Australia Limited, Melbourne, Australia

[21] Appl. No.: 131,389

[22] Filed: Mar. 17, 1980

[30] Foreign Application Priority Data

Mar. 19, 1979 [AU] Australia ............................... PD8094
Apr. 12, 1979 [GB] United Kingdom ............... 13065/79
May 22, 1979 [AU] Australia ............................... PD8886

[51] Int. Cl.³ ................. C07D 263/58; C07D 277/82; C07D 235/14; A01N 43/76
[52] U.S. Cl. ..................................... 548/222; 548/161; 548/305; 71/88; 71/90; 71/92; 71/95
[58] Field of Search ....................... 548/222, 161, 305

[56] References Cited

U.S. PATENT DOCUMENTS 3,594,373  7/1971  Stephens et al. ............. 548/222
4,130,413 12/1978  Handte et al. ............... 548/329

FOREIGN PATENT DOCUMENTS 2355092  5/1975  Fed. Rep. of Germany .
2640730  3/1978  Fed. Rep. of Germany .
2745869  4/1979  Fed. Rep. of Germany .
2815287 10/1979  Fed. Rep. of Germany .
1153647  5/1969  United Kingdom ............. 548/222
1153648  5/1969  United Kingdom .

Primary Examiner—Anton H. Sutto
Attorney, Agent, or Firm—Cushman, Darby & Cushman

[57] ABSTRACT

The invention concerns novel diarylamine derivatives of formula I

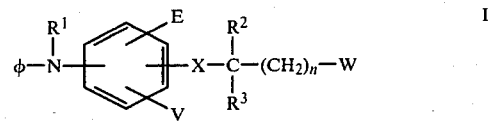

wherein φ is chosen from

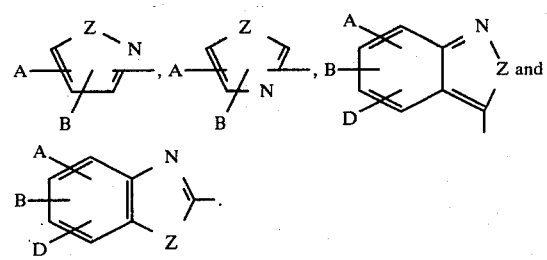

The compounds are herbicides and in further embodiments the invention provides herbicidal compositions containing as active ingredient a compound of formula I, a process for severely damaging or killing unwanted plants by applying to the plants or to the growth medium of the plants an effective amount of a compound of formula I, processes for the preparation of compounds of formula I and intermediates useful in the preparation of compounds of formula I.

6 Claims, No Drawings

PHENYLAMINE SUBSTITUTED ON AMINE WITH A BENZO(OXA, THIA OR DI) AZOLE GROUP

This invention relates to organic compounds having biological activity and in particular to organic compounds having herbicidal properties, to processes for the preparation of such compounds, to intermediates useful in the preparation of such compounds and to herbicidal compositions and processes utilizing such compounds.

We have now found a new class of diarylamine derivative which exhibit biological activity, and in particular herbicidal activity.

Accordingly the invention provides a compound of forumla I:

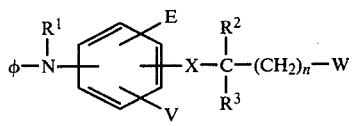

or a salt thereof wherein:

φ is chosen from the group consisting of

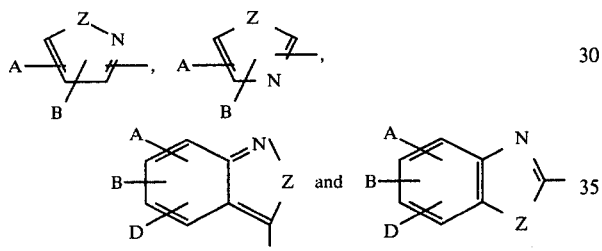

in which Z is chosen from O, S, NH and N—C$_1$–C$_6$ alkyl;

A, B, D, E and V are independently chosen from the group consisting of hydrogen, halogen, nitro, cyano, thiocyano, amino, C$_1$ to C$_6$ alkylamino, di(C$_1$ to C$_6$ alkyl)amino, C$_1$ to C$_6$ alkyl, C$_1$ to C$_6$ haloalkyl, C$_2$ to C$_6$ alkenyl, C$_3$ to C$_7$ cycloalkyl, C$_1$ to C$_6$ alkoxy, C$_1$ to C$_6$ haloalkoxy, C$_1$ to C$_6$ alkylthio, C$_1$ to C$_6$ alkylsulfinyl, C$_1$ to C$_6$ alkylsulfonyl, C$_1$ to C$_6$ haloalkylsulfinyl, C$_1$ to C$_6$ haloalkylsulfonyl, sulfo, C$_1$ to C$_6$ alkoxysulfonyl, sulfamoyl, N-(C$_1$ to C$_6$ alkyl)sulfamoyl, N,N-di(C$_1$ to C$_6$ alkyl)sulfamoyl, carboxy, (C$_1$ to C$_6$ alkoxy)carbonyl, carbamoyl, N-(C$_1$ to C$_6$ alkyl)carbamoyl, N,N-di(C$_1$ to C$_6$ alkyl)carbamoyl, phenyl, phenoxy, phenylthio, and the groups substituted phenyl, substituted phenoxy and substituted phenylthio wherein in each group the phenyl ring is substituted with one to three substituents chosen from the group consisting of halogen, C$_1$ to C$_6$ alkyl, C$_1$ to C$_6$ haloalkyl, C$_1$ to C$_6$ alkoxy, nitro and cyano;

R$^1$ is chosen from the group consisting of hydrogen, C$_1$ to C$_{10}$ alkyl, C$_2$ to C$_{10}$ alkenyl, C$_2$ to C$_{10}$ alkoxyalkyl, C$_1$ to C$_{10}$ haloalkyl, formyl, C$_2$ to C$_{10}$ alkanoyl, phenyl, benzyl, benzoyl, and the groups phenyl, benzyl and benzoyl wherein in each group the phenyl ring is substituted with one or two substituents chosen from the group consisting of halogen, C$_1$ to C$_6$ alkyl, C$_1$ to C$_6$ haloalkyl, C$_1$ to C$_6$ alkoxy, nitro and cyano;

R$^2$ is chosen from the group consisting of hydrogen, C$_1$ to C$_6$ alkyl, C$_2$ to C$_6$ alkenyl, C$_2$ to C$_6$ alkoxyalkyl, C$_1$ to C$_6$ haloalkyl, acetyl, propionyl, and C$_2$ to C$_6$ alkoxycarbonyl;

R$^3$ is chosen from the group consisting of hydrogen, C$_1$ to C$_6$ alkyl, C$_2$ to C$_6$ alkenyl, C$_2$ to C$_6$ alkoxyalkyl and C$_1$ to C$_4$ haloalkyl, or R$^2$ and R$^3$ together may form a methylene, ethylidene, propylidene or isopropylidene group;

W is chosen from the group consisting of cyano, thiocarbamoyl,

and CH$_2$Y wherein: G is chosen from the group consisting of hydroxy, mercapto, C$_1$ to C$_{10}$ alkoxy, C$_1$ to C$_{10}$ haloalkoxy, C$_2$ to C$_{10}$ alkenyloxy, C$_2$ to C$_{10}$ alkynyloxy, C$_1$ to C$_{10}$ alkylthio, C$_2$ to C$_{10}$ alkenylthio, C$_2$ to C$_{10}$ alkynylthio, C$_3$ to C$_7$ cycloalkoxy, C$_3$ to C$_7$ cycloalkoxy substituted with one or two C$_1$ to C$_4$ alkyl groups, phenoxy, phenylthio, benzyloxy, benzylthio, the group C$_1$ to C$_{10}$ alkoxy substituted with a substituent chosen from the group consisting of C$_1$ to C$_6$ alkoxy, amino, ammonio, cyano, N-(C$_1$ to C$_6$ alkyl)amino, N,N-di(C$_1$ to C$_6$ alkyl)amino and N,N,N-tri(C$_1$ to C$_6$ alkyl)ammonio, the groups phenoxy, phenylthio, benzyloxy and benzylthio wherein in each group the phenyl ring is substituted with one or two substituents chosen from the group consisting of halogen, nitro, cyano, C$_1$ to C$_6$ alkyl, C$_1$ to C$_6$ haloalkyl and C$_1$ to C$_6$ alkoxy, the group OM wherein M is the cation of an inorganic or organic base, the group —HNSO$_2$R$^4$ wherein R$^4$ is chosen from C$_1$ to C$_{10}$ alkyl and C$_1$ to C$_{10}$ haloalkyl, and the group —NR$^5$R$^6$ wherein R$^5$ and R$^6$ are independently chosen from the group consisting of hydrogen, C$_1$ to C$_6$ alkyl, phenyl and benzyl or R$^5$ and R$^6$ together form a heterocyclic ring; and Z is chosen from halogen, hydroxy, mercapto, C$_1$ to C$_{10}$ alkoxy, C$_1$ to C$_{10}$ haloalkoxy, C$_1$ to C$_{10}$ alkylthio and the group NR$^5$R$^6$ wherein R$^5$ and R$^6$ are as hereinbefore defined;

X is chosen from oxygen and sulfur; and n is 0, 1 or 2.

The compounds of formula I wherein R$^2$ and R$^3$ are not the same are optically active and the present invention also includes the individual stereo isomers of such compounds and mixtures of those stereo isomers in addition to the racemic mixture of stereo isomers.

Suitable A, B, D, E and V include hydrogen, halogen, nitro, cyano, thiocyano, amino, C$_1$ to C$_6$ alkylamino, di(C$_1$ to C$_6$ alkyl)amino, C$_1$ to C$_6$ alkyl, C$_1$ to C$_6$ haloalkyl, C$_2$ to C$_6$ alkenyl, C$_3$ to C$_7$ cycloalkyl, C$_1$ to C$_6$ alkoxy, C$_1$ to C$_6$ alkylthio, (C$_1$ to C$_6$ alkoxy)carbonyl, phenyl, phenoxy, phenylthio and the groups substituted phenyl, substituted phenoxy and substituted phenylthio wherein in each group the phenyl ring is substituted with one to three substituents chosen from the group consisting of halogen, C$_1$ to C$_6$ alkyl, C$_1$ to C$_6$ haloalkyl, C$_1$ to C$_6$ alkoxy, nitro and cyano.

Suitable R$^1$ include hydrogen, C$_1$ to C$_{10}$ alkyl, C$_2$ to C$_{10}$ alkenyl, C$_2$ to C$_{10}$ alkoxyalkyl, C$_1$ to C$_{10}$ haloalkyl, formyl, C$_2$ to C$_{10}$ alkanoyl, phenyl, benzyl, benzoyl and the groups phenyl, benzyl and benzoyl wherein in each group the phenyl ring is substituted with one or two substituents chosen from the group consisting of halogen, $C_1$ to $C_6$ alkyl, $C_1$ to $C_6$ haloalkyl, $C_1$ to $C_6$ alkoxy, nitro and cyano.

Suitable $R^2$ include hydrogen, $C_1$ to $C_6$ alkyl, $C_2$ to $C_6$ alkenyl, $C_2$ to $C_6$ alkoxyalkyl, $C_1$ to $C_6$ haloalkyl, acetyl, propionyl and $C_2$ to $C_6$ alkoxycarbonyl.

Suitable $R^3$ include hydrogen, $C_1$ to $C_6$ alkyl, $C_2$ to $C_6$ alkenyl, $C_2$ to $C_6$ alkoxyalkyl and $C_1$ to $C_6$ haloalkyl.

Suitable $R^2$ and $R^3$ together include methylene, ethylidene, propylidene and isopropylidene.

Suitable W include the groups cyano, thiocarbamoyl,

and —$CH_2Y$.

Suitable G include hydroxy, mercapto, $C_1$ to $C_{10}$ alkoxy, $C_1$ to $C_{10}$ haloalkoxy, $C_2$ to $C_{10}$ alkenyloxy, $C_2$ to $C_{10}$ alkynyloxy, $C_1$ to $C_{10}$ alkylthio, $C_2$ to $C_{10}$ alkenylthio, $C_3$ to $C_7$ cycloalkoxy, $C_3$ to $C_7$ cycloalkoxy substituted with one or two $C_1$ to $C_4$ alkyl groups, phenoxy, phenylthio, benzyloxy, benzylthio, the group $C_1$ to $C_{10}$ alkoxy substituted with a $C_1$ to $C_6$ alkoxy group, the groups phenoxy, phenylthio, benzyloxy and benzylthio wherein in each group the phenyl ring is substituted with one or two substituents chosen from the group consisting of halogen, nitro, cyano, $C_1$ to $C_6$ alkyl, $C_1$ to $C_6$ haloalkyl and $C_1$ to $C_6$ alkoxy, the group OM wherein M is the cation of an inorganic or organic base, the group —$NHSO_2R^4$ wherein $R^4$ is chosen from $C_1$ to $C_{10}$ alkyl and $C_1$ to $C_{10}$ haloalkyl, and group —$NR^5R^6$ wherein $R^5$ and $R^6$ are independently chosen from the group consisting of hydrogen, $C_1$ to $C_6$ alkyl, phenyl and benzyl or $R^5$ and $R^6$ together form a heterocyclic ring.

When G is the group OM suitable M include alkali metal ions, alkaline earth metal ions and the ammonium ion $HN^{\oplus}R^7R^8R^9$ wherein $R^7$, $R^8$ and $R^9$ are independently chosen from hydrogen, $C_1$ to $C_6$ alkyl, $C_2$ to $C_6$ hydroxyalkyl, phenyl and benzyl.

Suitable Y include halogen, hydroxy, mercapto, $C_1$ to $C_{10}$ alkoxy, $C_1$ to $C_{10}$ haloalkoxy, $C_1$ to $C_{10}$ alkylthio and the group —$NR^5R^6$ wherein $R^5$ and $R^6$ are independently chosen from the group consisting of hydrogen, $C_1$ to $C_6$ alkyl, phenyl and benzyl or $R^5$ and $R^6$ together form a heterocyclic ring.

When G or Y is the group —$NR^5R^6$ wherein $R^5$ and $R^6$ together form a heterocyclic ring suitable heterocyclic rings include morpholino, piperidino, 1-piperazinyl and 1-pyrrolidinyl.

Preferred $\phi$ include the group

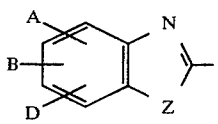

in which Z is chosen from O, S, NH and N-$C_1$ to $C_6$ alkyl.

Preferred A, B and D include hydrogen, halogen, nitro, $C_1$ to $C_6$ alkyl, $C_1$ to $C_6$ haloalkyl and $C_1$ to $C_6$ alkoxy.

Preferred E and V include hydrogen, halogen and nitro.

Preferred $R^1$ include hydrogen, $C_1$ to $C_6$ alkyl, $C_2$ to $C_6$ alkenyl, $C_2$ to $C_6$ alkynyl, $C_2$ to $C_6$ alkanoyl and benzyl.

Preferred $R^2$ and $R^3$ include hydrogen and $C_1$ to $C_6$ alkyl.

Preferred W are the groups:

(a)

wherein G is chosen from hydroxy, $C_1$ to $C_{10}$ alkoxy, $C_2$ to $C_{10}$ alkenyloxy, $C_2$ to $C_{10}$ alkynyloxy, $C_3$ to $C_7$ cycloalkoxy, benzyloxy, $C_1$ to $C_{10}$ alkylthio, amino, N-($C_1$ to $C_6$ alkyl)amino, N,N,-di($C_1$ to $C_6$ alkyl)amino, $C_1$ to $C_{10}$ alkoxy substituted with a substituent chosen from amino, ammonio, N-($C_1$ to $C_6$ alkyl)amino, N,N-di($C_1$ to $C_6$ alkyl)amino and N,N,N-tri($C_1$ to $C_6$ alkyl)ammonio, and the group OM wherein M is an alkali metal or alkaline earth metal ion; and (b) —$CH_2Y$ wherein Y is chosen from halogen, hydroxy, mercapto and $C_1$ to $C_{10}$ alkoxy.

Preferred X is oxygen.

Preferred n is 0 or 2.

Preferred compounds of the invention are those compounds of formula II

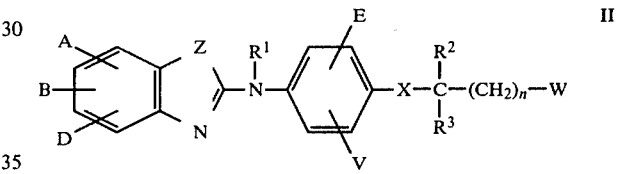

More preferred compounds of the invention include those in which:

A, B and D are indpendently chosen from hydrogen, halogen, nitro, $C_1$ to $C_6$ alkyl and $C_1$ to $C_6$ haloalkyl;

$R^1$ is chosen from hydrogen, $C_1$ to $C_6$ alkyl, $C_2$ to $C_6$ alkenyl, $C_2$ to $C_6$ alkynyl and benzyl;

$R^2$ is chosen from hydrogen and $C_1$ to $C_6$ alkyl;

$R^3$, E and V are hydrogen;

X is oxygen;

W is the group

wherein G is chosen from hydroxy, $C_1$ to $C_6$ alkoxy, $C_2$ to $C_6$ alkenyloxy and $C_2$ to $C_6$ alkynyloxy; and n is 0.

Even more preferred compounds of the invention include compounds of formula I in which:

$\phi$ is the group

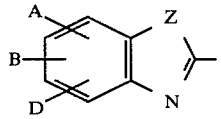

wherein

Z is oxygen or sulfur;

A is a 5- or 6-chloro, bromo or trifluoromethyl substituent;
$R^1$ is chosen from hydrogen and $C_1$ to $C_6$ alkyl;
$R^2$ is methyl;
$R^3$, B, D, E and V are hydrogen;
X is oxygen;
W is the group $$-\overset{O}{\underset{\|}{C}}-G$$

wherein G is chosen from hydroxy, cyclohexyloxy and $C_1$ to $C_8$ alkoxy; and
n is 0.

Examples of the compounds embraced by the invention include:

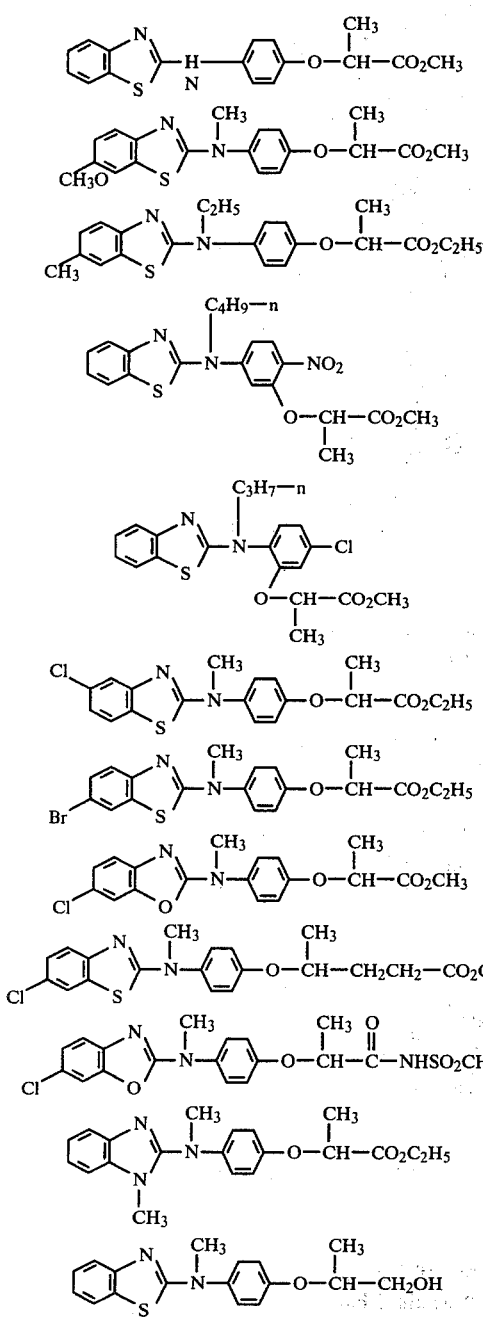

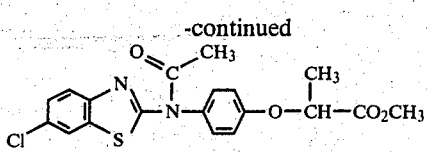

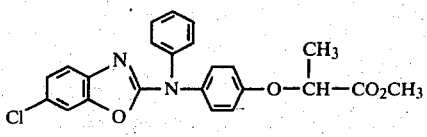

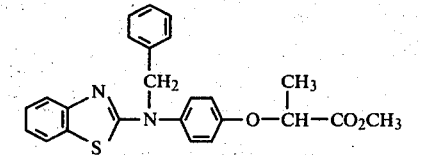

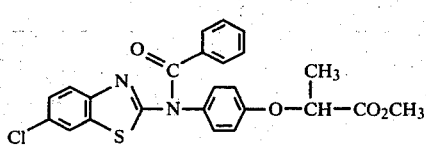

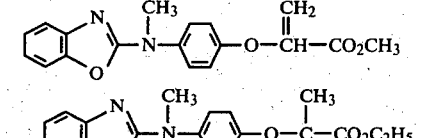

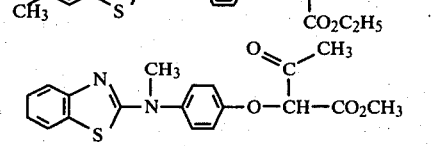

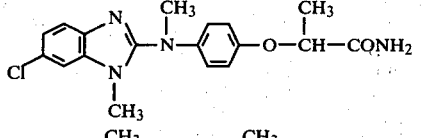

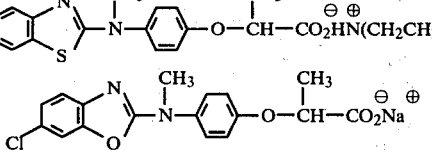

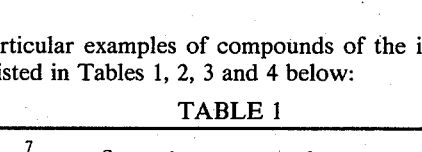

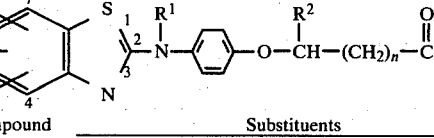

Particular examples of compounds of the invention are listed in Tables 1, 2, 3 and 4 below:

TABLE 1

| Compound No | A, B, D | $R^1$ | $R^2$ | n | G |
|---|---|---|---|---|---|
| 1 | all H | $CH_3$ | $CH_3$ | 0 | $CH_3O$ |
| 2 | 5-Cl | " | " | " | " |
| 3 | 7-Cl, 6-$C_2H_5O$ | " | " | " | $C_2H_5O$ |
| 4 | 5-$CF_3$ | " | " | " | " |
| 5 | 5-$CH_3$ | " | " | " | " |
| 6 | 4,6-$Cl_2$ | " | " | " | " |
| 7 | 7-Cl | " | " | " | " |
| 8 | 6-Cl, 4-$CH_3$ | " | " | " | " |
| 9 | 6-Cl | " | " | " | " |
| 10 | all H | " | " | " | " |
| 11 | all H | " | " | " | HO |
| 12 | 6-$NO_2$ | " | " | " | $C_2H_5O$ |

TABLE 2

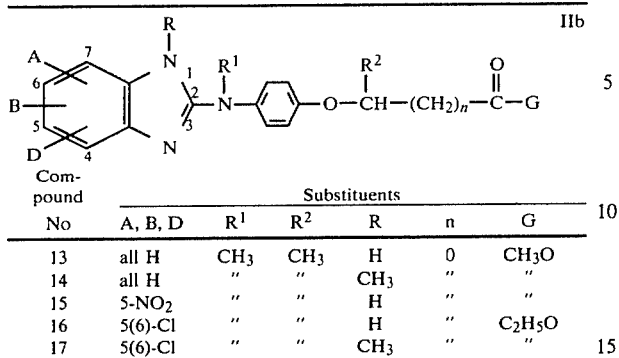

| Compound No | A, B, D | R¹ | R² | R | n | G |
|---|---|---|---|---|---|---|
| 13 | all H | $CH_3$ | $CH_3$ | H | 0 | $CH_3O$ |
| 14 | all H | " | " | $CH_3$ | " | " |
| 15 | 5-$NO_2$ | " | " | H | " | " |
| 16 | 5(6)-Cl | " | " | H | " | $C_2H_5O$ |
| 17 | 5(6)-Cl | " | " | $CH_3$ | " | " |

TABLE 3

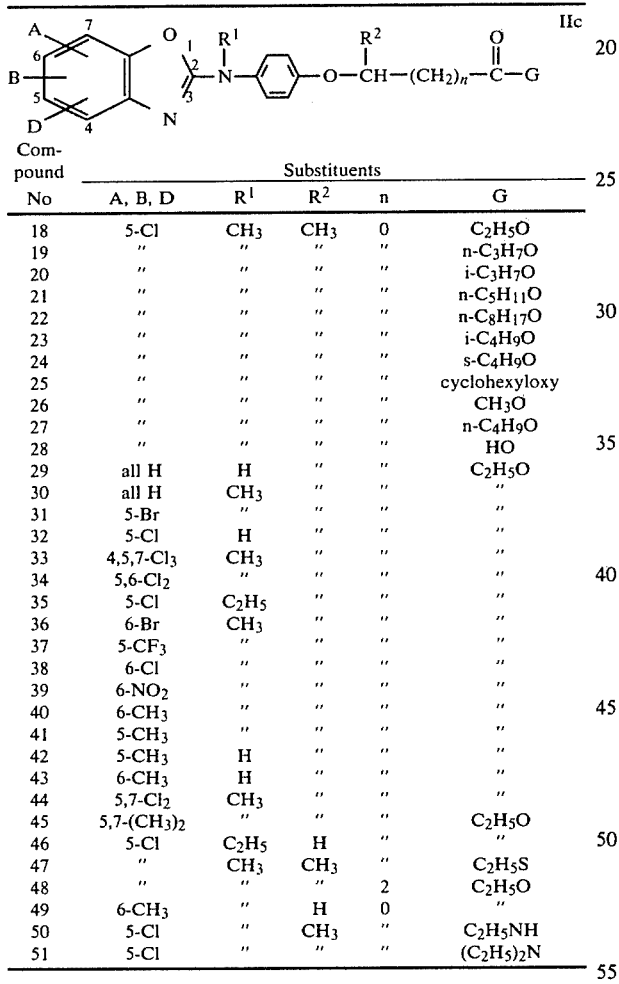

| Compound No | A, B, D | R¹ | R² | n | G |
|---|---|---|---|---|---|
| 18 | 5-Cl | $CH_3$ | $CH_3$ | 0 | $C_2H_5O$ |
| 19 | " | " | " | " | $n-C_3H_7O$ |
| 20 | " | " | " | " | $i-C_3H_7O$ |
| 21 | " | " | " | " | $n-C_5H_{11}O$ |
| 22 | " | " | " | " | $n-C_8H_{17}O$ |
| 23 | " | " | " | " | $i-C_4H_9O$ |
| 24 | " | " | " | " | $s-C_4H_9O$ |
| 25 | " | " | " | " | cyclohexyloxy |
| 26 | " | " | " | " | $CH_3O$ |
| 27 | " | " | " | " | $n-C_4H_9O$ |
| 28 | " | " | " | " | HO |
| 29 | all H | H | " | " | $C_2H_5O$ |
| 30 | all H | $CH_3$ | " | " | " |
| 31 | 5-Br | " | " | " | " |
| 32 | 5-Cl | H | " | " | " |
| 33 | 4,5,7-$Cl_3$ | $CH_3$ | " | " | " |
| 34 | 5,6-$Cl_2$ | " | " | " | " |
| 35 | 5-Cl | $C_2H_5$ | " | " | " |
| 36 | 6-Br | $CH_3$ | " | " | " |
| 37 | 5-$CF_3$ | " | " | " | " |
| 38 | 6-Cl | " | " | " | " |
| 39 | 6-$NO_2$ | " | " | " | " |
| 40 | 6-$CH_3$ | " | " | " | " |
| 41 | 5-$CH_3$ | " | " | " | " |
| 42 | 5-$CH_3$ | H | " | " | " |
| 43 | 6-$CH_3$ | H | " | " | " |
| 44 | 5,7-$Cl_2$ | $CH_3$ | " | " | " |
| 45 | 5,7-$(CH_3)_2$ | " | " | " | $C_2H_5O$ |
| 46 | 5-Cl | $C_2H_5$ | H | " | " |
| 47 | " | $CH_3$ | $CH_3$ | " | $C_2H_5S$ |
| 48 | " | " | " | 2 | $C_2H_5O$ |
| 49 | 6-$CH_3$ | " | H | 0 | " |
| 50 | 5-Cl | " | $CH_3$ | " | $C_2H_5NH$ |
| 51 | 5-Cl | " | " | " | $(C_2H_5)_2N$ |

TABLE 4

| Compound No | Structure |
|---|---|
| 52 | 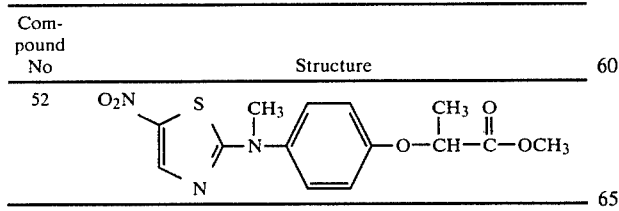 |

The compounds of the invention may be prepared by a variety of methods and in a further aspect the invention provides methods for the preparation of the compounds of formula I.

Compounds of formula Ia

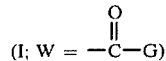

$$(I;\ W = -\overset{O}{\underset{\|}{C}}-G)$$

wherein G is not hydroxy may be prepared from the acid of formula Ib (I; $W=-CO_2H$) by any of the conventional methods known in the art for the conversion of a carboxylic acid to an acid salt, acid ester, acid amide or acid hydrazide (SCHEME A).

SCHEME A

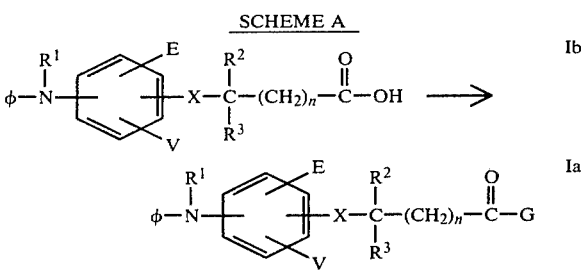

Compounds of formula Ic (I; $W=-C\equiv N$) may be prepared by any of the conventional methods known in the art for the conversion of an acid amide to the nitrile derivative of the acid (SCHEME B).

SCHEME B

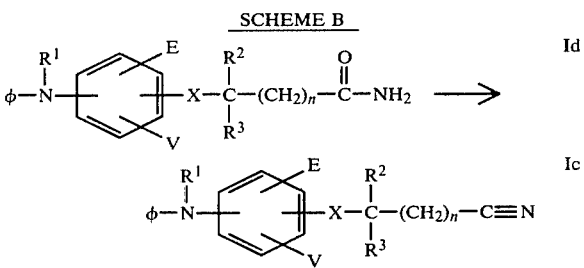

Compounds of formula Ie (I; $W=-CH_2OH$) may be prepared from the acid or acid esters of formula If (I; $W=$

wherein G=OH or O-alkyl) by any of the conventional methods known in the art for the conversion of an acid or acid ester to an alcohol (e.g. $LiAlH_4$ reduction). (SCHEME C).

SCHEME C

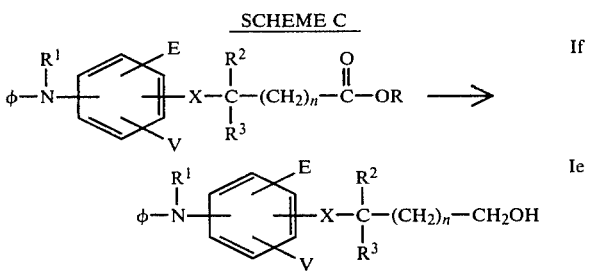

Alcohols of formula Ie (I; $W=-CH_2OH$) may be converted to alkyl halides (I; $W=-CH_2$-halogen) and ethers or thioethers (I; W=—CH$_2$OR or —CH$_2$SR) by any of conventional methods known in the art.

Amines of formula Ig (I; W=—CH$_2$NR$^5$R$^6$) may be prepared either from the alkyl halides (I; W=—CH$_2$-halogen) or by reduction of the amides

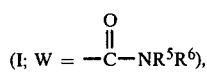

(I; W = —C—NR$^5$R$^6$), both conventional processes known in the art.

Compounds of formula I wherein R$^1$ is not hydrogen may be prepared from compounds of formula I wherein R$^1$ is hydrogen by any of the conventional methods known in the art for the preparation of derivatives of secondary amines (eg alkylation and acylation).

Compounds of formula I wherein $\phi$, A, B, D, E, V, X, R$^1$, R$^2$, R$^3$, W and n are as hereinbefore defined may be prepared by the condensation of a phenol or thiophenol of formula IX with a compound of formula X wherein hal is chlorine, bromine or iodine, preferably in the presence of an alkaline material; according to SCHEME D.

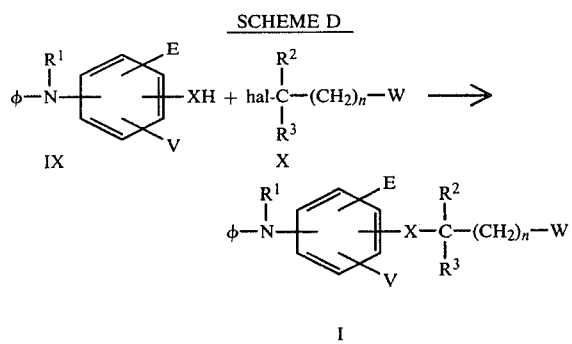

Compounds of formula I may also be prepared by:

(a) the condensation of the appropriate heteroaryl compound of formula V, wherein L is a leaving group (for example, alkylthio, alkylsulfonyl, chlorine, bromine or iodine) with the appropriate aniline of formula VI according to SCHEME E.

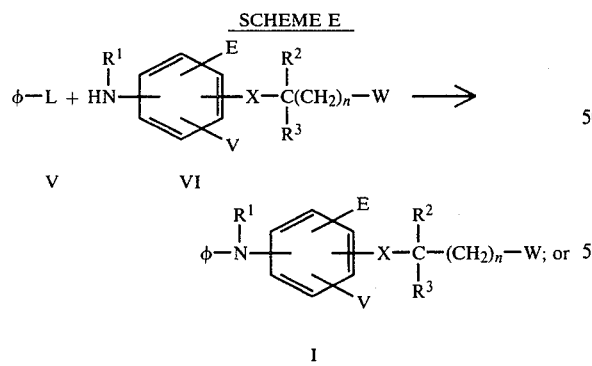

(b) the following steps in sequence:
(i) the condensation of the appropriate heteroaryl compound of formula V, wherein L is a leaving group (for example alkylthio, alkylsulfonyl, chlorine, bromine or iodine) with the appropriate aniline of formula VII, wherein Q is hydroxy, mercapto, C$_1$ to C$_6$ alkoxy or C$_1$ to C$_6$ alkylthio to give a compound of formula VIII wherein Q is hydroxy, mercapto, C$_1$ to C$_6$ alkoxy or C$_1$ to C$_6$ alkylthio;

(ii) the dealkylation of the compound of formula VIII prepared in step (i) above wherein Q is C$_1$ to C$_6$ alkoxy or C$_1$ to C$_6$ alkylthio to give a product of general formula IX; and (iii) the condensation of product of formula IX obtained in step (i) or step (ii) above with a compound of formula X according to the process described for SCHEME D above. (Steps (i) and (ii) are shown in SCHEME F).

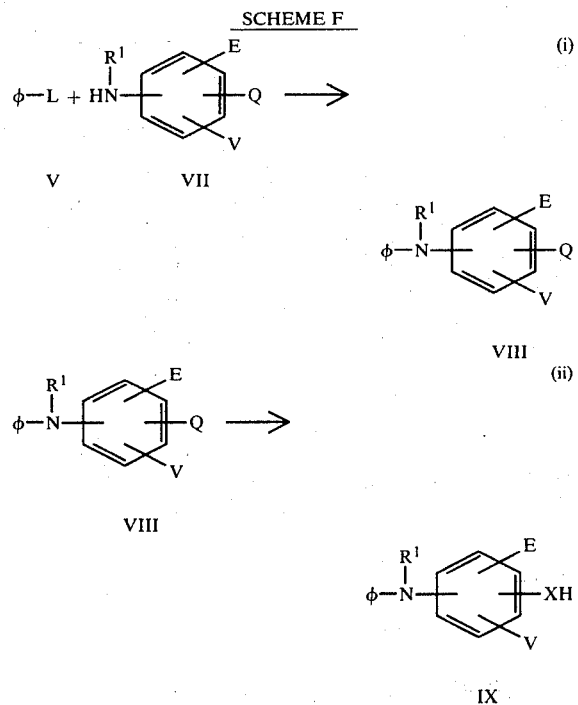

The condensation reaction illustrated in SCHEME D and outlined above is preferably carried out in the presence of an alkaline material and preferably in the presence of a solvent. Suitable alkaline materials include, for example, the alkali and alkaline earth metal hydroxides and carbonates such as sodium hydroxide, potassium hydroxide, sodium carbonate and potassium carbonate. Suitable solvents include ketones such as, for example, acetone, methyl ethyl ketone and methyl isobutyl ketone, and dipolar aprotic solvents such as, for example, dimethylformamide, dimethylacetamide, dimethylsulfoxide, N-methylpyrrolidone, hexamethylphosphoramide and sulfolan.

The condensation reactions illustrated in SCHEMES E and F and outlined above are preferably carried out in the presence of a solvent.

The reaction conditions required to effect the condensation reactions illustrated in SCHEMES D, E, and F and outlined above vary according to the nature of the reactants and the solvent used. In general the reaction is facilitated by the application of heat and usually a reaction temperature in the range of 40° to 150° C. and reaction time of between 0.5 and 20 hours is satisfactory. However, higher or lower reaction temperatures and/or shorter or longer reaction times may be used if desired.

The dealkylation reaction illustrated in SCHEME F and outlined in paragraph (b)(ii) above may be effected using a variety of reagents known in the art. For example, aryl-alkyl ethers may be cleaved using reagents such as pyridine hydrochloride, hydriodic acid, hydrobromic acid, sodium thioethoxide in dimethylformamide, acetyl p-toluenesulphonate, sodium or potassium iodide in formic or acetic acid, lithium iodide in 2,4,6-collidine and boron tribromide. Reaction times and reaction conditions vary widely depending on the dealkylation agent used and the ether to be cleaved. The reaction conditions generally employed when using the above "ether-cleavage" reagents are known to those skilled in the art and may be adapted without undue experimentation to effect the "ether-cleavage" reaction illustrated in SCHEME F and outlined in paragraph (b)(ii) above.

The compounds of formula VIII

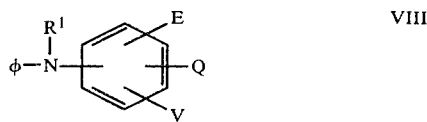

VIII which are useful intermediates in the preparation of compounds of formula I, are believed to be novel compounds. Therefore, in a further embodiment the invention provides compounds of formula VIII wherein $\phi$, $R^1$, E, V and Q are as hereinbefore defined.

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against a variety of plants. However, certain of the compounds of the invention are selectively active agains monocotyledonous plants, dicotyledonous plants being relatively unaffected by rates of application of the compounds of the invention which are severely damaging or lethal to other plant species. Therefore, in yet a further aspect the invention provides a process for selectively controlling the growth of weeds in crops which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (pre-emergence application).

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides plant growth inhibiting, plant damaging, or plant killing compositions comprising a compound of formula I as hereinbefore defined and an inert carrier therefor.

Compositions according to the invention include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01 to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, eg kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type. The cationic agents are, for example, quaternary ammonium compounds (eg cetyltrimethylammonium bromide). Suitable anionic agents are soaps; salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl- and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl-phenol or octylcresol. Other non-ionic agents are the partial esters derived from long chain fatty acids and hexitol anhydrides, for example sorbitan monolaurate; the condensation products of the partial ester with ethylene oxide; and the lecithins.

The aqueous solutions or dispersions may be prepared by dissolving the active ingredient in water or an organic solvent optionally containing wetting or dispersing agent(s) and then, when organic solvents are used, adding the mixtures so obtained to water optionally containing wetting or dispersing agent(s). Suitable organic solvents include, for example, ethylene dichloride, isopropyl alcohol, propylene glycol, diacetone alcohol, toluene, kerosene, methylnapthalene, the xylenes and trichloroethylene.

The compositions for use in the form of aqueous solutions or dispersions are generally supplied in the form of a concentrate containing a high proportion of the active ingredient, and the concentrate is then diluted with water before use. These concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited the formulation selected for use and whether the compound is to be applied for foliage or root uptake. As a general guide, however, an application rate of from 0.05 to 20 kilograms per hectare is suitable while from 0.1 to 10 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may be insufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3-thiadiazin-4-one-2,2-dioxides such as 3-isopropylbenzo-2,1,3-thiadiazin-4-one-2,2-dioxide (common name bentazon);

B. hormone herbicides and in particular the phenoxyalkanoic acids such as 4-chloro-2-methylphenoxyacetic acid (common name MCPA), 2-(2,4-dichlorophenoxy)propionic acid (common name dichlorprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);

C. 3-[4-(4-halophenoxy)phenyl]-1,1-dialkylureas such as 3-[4-(4-chlorophenoxy)phenyl]1,1-dimethylurea (common name chloroxuron);

D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;

E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);

F. phenylurea herbicides such as N'-(3,4-dichlorophenyl)-N,N-dimethylurea (common name diuron) and N,N-dimethyl-N'-[3-(trifluoromethyl)phenyl]urea (common name fluometuron);

G. phenylcarbamoyloxyphenylcarbamates such as 3-[(methoxycarbonyl)amino]phenyl (3-methylphenyl)-carbamate (common name phenmedipham) and 3-[(ethoxycarbonyl)amino]phenyl phenylcarbamate (common name desmedipham);

H. 2-phenylpyridazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);

J. triazine herbicides such as 2-chloro-4-ethylamino-6-(iso-propylamino)-1,3,5-triazine (common name atrazine), 2-chloro-4,6-di(ethylamino)-1,3,5-triazine (common name simazine) and 2-azido-4-(iso-propylamino)-6-methylthio-1,3,5-triazine (common name aziprotryne);

K. 1-alkoxy-1-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. thiolcarbamate herbicides such as S-propyl dipropylthiocarbamate (common name vernolate);

M. 1,2,4-triazin-5-one herbicides such as 4-amino-4,5-dihydro-3-methyl-6-phenyl-1,2,4-l-triazine-5-one (common name metamitron) and 4-amino-6-tert-butyl-4,5-dihydro-3-methylthio-1,3,4-triazin-5-one (common name metribuzin);

N. Benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben).

O. anilide herbicides such as N-butoxymethyl-α-chloro-2',6'-diethylacetanilide (common name butachlor) the corresponding N-methoxy compound (common name alachlor), the corresponding N-iso-propyl compound (common name propachlor) and 3',4'-dichloropropionanilide (common name propanil);

P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil).

Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether; and S. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

T. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

U. organoarsenical herbicides such as monosodium methanearsonate (common name MSMA); and V. amino acid herbicides such as N-(phosphonomethyl)glycine (common name glyphosate) and its salts and esters.

The invention is now illustrated by, but in no way limited to, the following Examples.

EXAMPLE 1

Preparation of Methyl 2-{4-[N-methyl-N-(5-chloro-2-benzothiazolyl)amino]phenoxy}propionate (2)

(a) 2,5-Dichlorobenzothiazole 5-Chloro-2-mercaptobenzothiazole (10.0 g) was added to sulfuryl chloride (50 ml) and the mixture was stirred at room temperature for a period of 1 hr. Excess sulfuryl chloride in the mixture was destroyed by the addition of water and the aqueous mixture was extracted with dichloromethane. The organic extract was washed with water, dried over anhydrous magnesium sulfate and passed through a short column of silica gel. The solvent was removed by distillation under reduced pressure to give 2,5-dichlorobenzothiazole (10.0 g) as pale yellow crystals, mp 70° C.

(b) 4-[N-methyl-N-(5-chloro-2-benzothiazolyl)amino]phenol 2,5-Dichlorobenzothiazole (5.0 g) and 4-(N-methylamino)phenol (4.7 g) were added to a water/acetonitrile mixture (1:1) and the mixture was heated under reflux for a period of 24 hours. After cooling the solid was collected by filtration and recrystallised from water/acetonitrile to give 4-[N-methyl-N-(5-chloro-2-benzothiazolyl)amino]phenol (5.0 g) as colourless crystals, mp 238°–240° C.

(c) Methyl 2-{4-[N-methyl-N-(5-chloro-2-benzothiazolyl)amino]phenoxy}propionate (2)

A mixture of 4-[N-methyl-N-(5-chloro-2-benzothiazolyl)amino]phenol (2.0 g), methyl 2-bromopropionate (1.16 g), potassium carbonate (1.05 g) and dimethylformamide was heated at a temperature of 100° C. for a period of 1 hr with vigorous stirring. After cooling the mixture was poured into water and the aqueous mixture was extracted with dichloromethane. The organic extract was washed with water, dried over anhydrous magnesium sulfate and the solvent was removed by distillation under reduced pressure. The residue was recrystallised from methanol to give methyl 2-{4-[N-methyl-N-(5-chloro-2-benzothiazolyl)amino]phenoxy}propionate (1.55 g) as colourless crystals, mp 120° C.

EXAMPLE 2

The compounds no 1, 3, 4, 5, 6, 7, 8 and 9 (see Table 1) were prepared following essentially the same procedure as that described in Example 1. The pmr spectrum of each of the compounds was consistent with the assigned structure and details of the spectra of the compounds, or the boiling point or the melting point of the compounds, are recorded in Example 16, Table 5.

EXAMPLE 3

Preparation of Methyl 2-{4-[N-methyl-N-(2-benzimidazolyl)amino]phenoxy}propionate (13)

(a) Benzimidazolin-2-one

A mixture of o-phenylenediamine (15.0 g) and urea (50.0 g) was heated at a temperature of 170° C. for a period of 45 min. The solid product was washed with water and recrystallised from ethanol to give benzimidazolin-2-one (16.3 g) as colourless crystals, mp>260° C.

(b) 2-Chlorobenzimidazole

Benzimidazolin-2-one (13.0 g) was added to phosphoryl chloride and the mixture was heated under reflux for a period of 3.5 hours. The excess phosphoryl chloride was removed by distillation and the residue was treated with water. The acidic solution was cooled, filtered and made basic by the addition of dilute ammonium hydroxide. The solid was collected and recrystallised from aqueous ethanol to give 2-chlorobenzimidazole (11.5 g) as colourless needles, mp 214° C.

(c) 4-[N-Methyl-N-(2-benzimidazolyl)amino]phenol.

A mixture of 2-chlorobenzimidazole (1.0 g), 4-(N-methylamino)phenol (1.13 g) and acetonitrile/water (1:1) was heated under reflux for a period of 5 hours. The mixture was concentrated, made basic with dilute ammonium hydroxide and the solid was collected. The product was recrystallised from ethanol to give 4-[N-methyl-N-(2-benzimidazolyl)amino]phenol (0.92 g) as colourless crystals, mp>260° C.

(d) Methyl 2-{4-[N-methyl-N-(2-benzimidazolyl)amino]phenoxy}propionate (13)

A mixture of 4-[N-methyl-N-(2-benzimidazolyl)amino]phenol (1.14 g), methyl 2-bromopropionate (0.80 g), anhydrous potassium carbonate (0.72 g) and dimethylformamide (25 ml) was heated for 4 hours at a temperature of 100° C. with vigorous stirring. After cooling, the mixture was poured into water and the aqueous solution was extracted with dichloromethane. The organic extract was washed with water, dried over anhydrous magnesium sulfate and the solvent was removed by distillation under reduced pressure. The residue was purified by chromatography over silica gel with dichloromethane elution to give methyl 2-{4-[N-methyl-N-(2-benzimidazolyl)amino]phenoxy}propionate (1.0 g) as a colourless oil. The pmr spectrum of the compound was consistent with the assigned structure (CDCl$_3$; chemical shift δppm): 1.50, d, 3H; 3.35, s, 3H; 3.70, s, 3H; 4.60, q, 1H; 6.50–7.60, m, 9H.

EXAMPLE 4

The compounds no 15 and 16 (see Table 1) were prepared following essentially the same procedure as that described in Example 3. The pmr spectrum of each compound was consistent with the assigned structure and details of the spectra are recorded in Example 16, Table 5.

EXAMPLE 5

Preparation of Methyl 2-{4-[N-methyl-N-(1-methyl-2-benzimidazolyl)amino]phenoxy}propionate (14)

A mixture of methyl 2-{4-[N-methyl-N-(2-benzimidazolyl)amino]phenoxy}propionate (0.66 g) and dimethylformamide (25 ml) was treated with sodium hydride (0.11 g). Methyl iodide (0.3 g) was added and the mixture was stirred at room temperature for a period of 30 minutes. Water was added to the mixture and the aqueous solution was extracted with diethyl ether. The organic extract was washed with water, dried over anhydrous magnesium sulfate and the solvent was removed by distillation under reduced pressure. The residue was purified by chromatography over silica gel with dichloromethane elution to give methyl 2-{4-[N-methyl-N-(2-benzimidazolyl)amino]phenoxy}propionate as a pale yellow oil (0.50 g). The pmr spectrum of the product was consistent with the assigned structure (CDCl$_3$; chemical shift δppm): 1.50, d, 3H; 3.10, s, 3H; 3.35, s, 3H; 3.70, s, 3H; 4.60, q, 1H; 6.50–7.60, m, 8H.

EXAMPLE 6

Compound no 17 (see Table 1) was prepared following essentially the same procedure as that described in Example 5. The pmr spectrum of the compound was consistent with the assigned structure and details of the spectrum are recorded in Example 16, Table 5.

EXAMPLE 7

Preparation of Ethyl 2-{4-[N-methyl-N-(5-chloro-2-benzoxazolyl)amino]-phenoxy}propionate (18)

(a) 4-[N-Methyl-N-(5-chloro-2-benzoxazolyl)amino]-phenol

A solution of the sulfate salt of 4-(N-methylamino)-phenol (0.008 mol, 2.76 g) in methyl ethyl ketone (25 ml) containing pure potassium carbonate (0.008 mol, 1.1 g) was warmed to reflux and a solution of 2,5-dichlorobenzoxazole (0.016 mol, 3.0 g) in methyl ethyl ketone (25 ml) was added dropwise over 2 hours. The resulting mixture was heated at reflux for a further hour, stood overnight, then stirred at room temperature for a further 8 hours. The solvent was then evaporated leaving a white solid. This was treated with a mixture of water (25 ml) and saturated aqueous sodium carbonate solution (25 ml). The solid was collected, washed with water, dried by suction and recrystallised three times from boiling toluene. Yield 1.4 g, mp 216°–217° C.; ir and pmr spectra and analysis consistent with assigned structure.

(b) Ethyl 2-{4-[N-methyl-N-(5-chloro-2-benzoxazolyl)amino]phenoxy}propionate (18)

4-[N-Methyl-N-(5-chloro-2-benzoxazolyl)amino]-phenol (0.00255 mol, 0.7 g, prepared as above), ethyl 2-bromopropionate (0.00255 mol, 0.46 g) and potassium carbonate (0.00255 mol, 0.35 g) were mixed in methyl ethyl ketone (5 ml) and heated under reflux for 6 hours. The solvent was then evaporated, the residue taken into water (25 ml) and twice extracted with diethyl ether (25 ml). An oily residue was obtained which was purified by preparative thin layer chromatography on silica gel, eluent toluene/diethyl ether. Yield 0.75 g, mp 68.0°–68.6° C.; ir, and pmr spectra and analysis consistent with assigned structure.

EXAMPLE 8

The compounds no 10 and 12 inclusive, 19 to 27 inclusive, 29 to 35 inclusive, 38 to 47 inclusive and 49 (see Tables 1, 3) were prepared following essentially the same procedure as that described in Example 7. The ir and pmr spectra and analysis of each compound were consistent with the assigned structure.

EXAMPLE 9

Preparation of 2-{4-[N-Methyl-N-(5-chloro-2-benzoxazolyl)amino]-phenoxy}propionic acid (28)

Ethyl 2-{4-[N-methyl-N-(5-chloro-2-benzoxazolyl)amino]phenoxy}propionate (10.0 g; see Example 7) was suspended in isopropyl alcohol (50 ml) and a solution of sodium hydroxide (1.12 g) in water (50 ml) was added over a period of 45 minutes. Further isopropyl alcohol (60 ml) was added and the mixture was stirred at room temperature for a period of 48 hours. The alcohol was removed by distillation under reduced pressure, the residue was dissolved in water and the aqueous solution was acidified to pH 4 by the addition of aqueous 2 M hydrochloric acid. The precipitate was collected by filtration, dried and recrystallised from ethyl acetate to give the title compound (5.83 g; 63%), mp 152°–154° C. The pmr spectrum of the compound was consistent with the assigned structure.

EXAMPLE 10

Preparation of Ethyl 2-{4-[N-methyl-N-(6-bromo-2-benzoxazolyl)amino]-phenoxy}propionate (36)

(a) 2-(Methylthio)benzoxazole

2-Mercaptobenzoxazole (6.0 g, 0.04 mole) was slowly added, with stirring, to a solution of sodium methoxide prepared by the addition of sodium (1.0 g) to anhydrous methanol (150 ml). Methyl iodide (5 ml) was added and the mixture was stirred at a temperature of 50° C. for a period of 3 hours and allowed to stand overnight at room temperature. The methanol was removed by distillation under reduced pressure and the solid residue was triturated with ice water and the insoluble material was collected by filtration. The solid was dissolved in chloroform, dried over anhydrous magnesium sulfate and the solvent removed to give 2-(methylthio)benoxazole (5.8 g) as a brown oil.

(b) 6-Bromo-2-(methylthio)benzoxazole 2-(Methylthio)benzoxazole (5.8 g, see (a) above) was dissolved in chloroform (75 ml) and a solution of bromine (6.0 g) in chloroform (30 ml) was added dropwise, with stirring, over a period of 45 minutes. The mixture was allowed to stand overnight at room temperature and the solvent removed by distillation under reduced pressure to give a brown oil. The oil was washed with aqueous sodium metabisulfite and crystallised from ethanol/water to give the title compound as pink platelets (2.0 g), mp 95°–96° C.

4-[N-Methyl-N-(6-bromo-2-benzoxazolyl)amino]-phenol

An intimate mixture of 4-(N-methylamino)phenol acetate (7.3 g, 0.04 mole) and 6-bromo-2-(methylthio)-benzoxazole (6.0 g, 0.025 mole) was prepared and heated on an oil bath to a temperature of 180° C. The mixture was heated at this temperature for a period of 4 hours during which time acetic acid distilled from the mixture and methyl mercaptan was evolved and was trapped in aqueous sodium hydroxide. The mixture was cooled to form a solid and the solid was extracted with hot toluene (4×100 ml). The toluene solution was filtered hot and the solvent removed by distillation to give a brown solid. The solid was recrystallised from toluene to give the title compound as a grey solid (3.5 g), mp 195° C.

(d) Ethyl 2-{4-[N-methyl-N-(6-bromo-2-benzoxazolyl)amino]phenoxy}propionate (36)

A mixture of 4-[N-methyl-N-(6-bromo-2-benzoxazolyl)amino]phenol (0.6, 0.002 mole), ethyl 2-bromopropionate (0.4 g, 0.002 mole), anhydrous potassium carbonate (0.3 g, 0.002 mole) and methyl ethyl ketone (6 ml) was heated under reflux, with stirring, for a period of 3 hours. Thin layer chromatography indicated that the reaction had not gone to completion and therefore further anhydrous potassium carbonate (0.15 g) and methyl ethyl ketone was added and the mixture was heated under reflux for a further period of 3 hours. The solvent was removed by distillation under reduced pressure, water (50 ml) was added to the residue and the aqueous mixture was extracted with diethyl ether (3×30 ml). The combined extracts were washed with brine, dried over anhydrous magnesium sulfate and the solvent was evaporated to give a dark red oil. The oil was heated at a temperature of 100° C. at a pressure of 0.1 mm Hg for a period of 2 hours to remove residual ethyl 2-bromopropionate and the residue was recrystallised from hexane/cyclohexane to give the title compound as a white solid (0.45 g), mp 91°–92° C.

EXAMPLE 11

Preparation of Ethyl 2-{4-[N-methyl-N-(5-trifluoromethyl-2-benzoxazolyl)amino]phenoxy}propionate (37)

(a) 2-Nitro-4-trifluoromethylphenol

Powdered sodium hydroxide (48 g) was added in portions over a period of 24 hours to a stirred solution of 4-chloro-3-nitrobenzotrifluoride (90 g) in dimethylsulfoxide (120 ml). After stirring the mixture vigorously for a further day another portion of powdered sodium hydroxide (4.8 g) was added and stirring was continued for a further 8 hours period. The mixture was poured into cold water (1 litre) and extracted with diethyl ether. The aqueous phase was acidified with concentrated hydrochloric acid, extracted with diethyl ether and the ethereal phase was washed with brine. The washed ethereal solution was dried over anhydrous magnesium sulfate and the solvent was evaporated to give the title compound as a brown oil (50 g).

(b) 2-Amino-4-trifluoromethylphenol

Sodium dithionite (97.0 g, 0.5 mole) was added in portions over a period of 6 hours to a solution of 2-nitro-4-trifluoromethylphenol (31 g, 0.15 mole) in a mixture of ethanol (120 ml) and water (90 ml), the solution being heated, with stirring, at a temperature of 55° C. during the addition. The mixture was filtered, the filtrate retained, and the collected solid was triturated with ethanol and refiltered. The solvent was removed from the combined filtrates by distillation under reduced pressure to give a yellow solid. The solid was dissolved in water, the aqueous solution extracted with diethyl ether (4×100 ml) and the combined ethereal phases were washed with brine. The ethereal phase was dried over anhydrous magnesium sulfate and the solvent evaporated to give a yellow solid which was recrystallised from petroleum ether (700 ml, bp 100°–120° C.) to give the title compound as a pale yellow solid (10.6 g).

(c) 2-Mercapto-5-trifluoromethylbenzoxazole

A mixture of 2-amino-4-trifluoromethylphenol (8.85 g, 0.05 mole), potassium ethyl xanthate (8.8 g, 0.055 mole) and ethanol was heated under gentle reflux for a period of 24 hours. After cooling, the mixture was filtered and the filtrate was distilled under reduced pressure to remove the solvent and to give an orange solid. The solid was dissolved in water, the aqueous solution extracted with ethyl acetate and the organic phase evaporated to give a red wolid. The solid was triturated with boiling petroleum ether (bp 100°–120° C.) and the insoluble material collected by filtration to give the title compound (3.5 g).

(d) 2-(Methylmercapto)-5-trifluoromethylbenzoxazole.

2-Mercapto-5-trifluoromethylbenzoxazole (8.8 g, 0.04 mole) was added slowly to a stirred solution of sodium (1.0 g, 0.43 mole) in anhydrous methanol (150 ml). Methyl iodide (5 ml) was added to the stirred solution over a period of 5 minutes, the mixture was stirred at room temperature for a period of 3 hours and then allowed to stand overnight. The mixture was filtered and the solvent was evaporated to give an orange solid. The solid was recrystallised from ethanol/water to give the title compound as a yellow solid (2.3 g).

(e) 4-[N-Methyl-N-(5-trifluoromethyl-2-benzoxazolyl)amino]phenol.

A mixture of 2-(methylmercapto)-5-trifluoromethylbenzoxazole (2.2 g, 0.01 mole) and 4-(N-methylamino)phenol acetate (3.7 g, 0.2 mole) was heated on an oil bath at a temperature of 200° C. for a period of 3 hours. During this period acetic acid distilled from the mixture and methyl mercaptan was evolved and was trapped in aqueous sodium hydroxide. The reaction mixture was cooled and the dark solid was triturated with boiling toluene (3×100 ml). The toluene extracted were filtered, combined and the toluene was evaporated under reduced pressure to give the title compound (2.0 g) as a brown oil.

(f) Ethyl 2-{4-[N-methyl-N-(5-trifluoromethyl-2-benzoxazolyl)amino]phenoxy}propionate (37)

A mixture of 4-[N-methyl-N-(5-trifluoromethyl-2-benzoxazolyl)amino]phenol (1.8 g, 0.006 mole), ethyl 2-bromopropionate (1.2 g, 0.006 mole), ethyl 2-bromopropionate (1.2 g, 0.006 mole), anhydrous potassium carbonate (0.9 g, 0.006 mole) and methyl ethyl ketone (25 ml) was heated under reflux, with stirring, for a period of 7 hours and then allowed to stand at room temperature for a period of 48 hours. The solvent was removed by distillation under reduced pressure and the residue was triturated with a mixture of water and diethyl ether. The combined ethereal extracts (200 ml) were washed with brine, dried over anhydrous magnesium sulfate and the ether evaporated to give a yellow oil. The oil was chromatographed over silica gel (eluant diethyl ether) to give the title compound as a yellow oil (0.8 g).

EXAMPLE 12

Ethyl 4-{4-[N-methyl-N-(5-chloro-2-benzoxazolyl)amino]phenoxy}valerate (48)

A mixture of 4-[N-methyl-N-(5-chloro-2-benzoxazolyl)amino]phenol (1.0 g, 0.0039 mole; see Example 7 part (a), ethyl 4-bromovalerate (0.89 g, 0.0043 mole), anhydrous potassium carbonate (0.54 g) and methyl isobutyl ketone (15 ml) was heated under reflux for a period of 30 hours with further portions (0.05 g) of anhydrous potassium carbonate being added at 3 hour intervals. The reaction mixture was cooled, filtered and the filtrate was distilled under reduced pressure to remove the solvent. The residue (a red oil) was distilled under reduced pressure, bp 240°–260° C. at 0.04 mm Hg and the distillate was further purified by preparative thin layer chromatography on silica gel (eluent chloroform/ethanol 15:1) to give the title compound (0.47 g) as a red oil. The pmr and mass spectra of the compound were consistent with the assigned structure.

EXAMPLE 13

Preparation of N-Ethyl 2-{4-[N-methyl-N-(5-chloro-2-benzoxazolyl)amino]phenoxy}propionamide (50)

(a) 2-{4-[N-Methyl-N-(5-chloro-2-benzoxazolyl)amino]phenoxy}propionyl chloride

A mixture of 2-{4-[N-methyl-N-(5-chloro-2-benzoxazolyl)amino]phenoxy}propionic acid (3.0 g, 0.0087 mole; see Example 9), thionyl chloride (0.76 ml, 0.01 mole) and chloroform (25 ml) was heated under reflux for a period of 3 hours. The reaction mixture was cooled and the solvent and excess thionyl chloride was removed by distillation under reduced pressure to give the title compound.

(b) N-Ethyl 2-{4-[N-methyl-N-(5-chloro-2-benzoxazolyl)amino]phenoxy}propionamide (50)

A mixture of 70% aqueous ethylamine (0.46 g) and dichloromethane (5 ml) was cooled, with stirring, in an ice bath. A solution of the acid chloride (1.05 g; prepared as described in part (a) above) in dichloromethane (5 ml) was added and the mixture was stirred for 7 hours and then allowed to stand overnight. After this time thin layer chromatography indicated that the reaction had not gone to completion and therefore a further portion of 70% aqueous ethylamine was added and the mixture was heated under reflux for a period of 3 hours. The mixture was allowed to cool, made up to 30 ml with dichloromethane and was washed with water (4×20 ml). The organic phase was dried over anhydrous magnesium sulfate and the solvent removed by evaporation. The solid residue was purified by preparative thin layer chromatography on silica gel (eluent dichloromethane/isopropyl alcohol 20:1) to give the title compound (0.74 g), mp 141°–142° C. The pmr spectrum of the compound was consistent with the assigned structure.

EXAMPLE 14

N,N-Diethyl 2-{4-[N-methyl-N-(5-chloro-2-benzoxazolyl)amino]phenoxy}propionamide (51) was prepared from diethylamine and 2-{4-[N-methyl-N-(5-chloro-2-benzoxazolyl)amino]phenoxy}propionyl chloride following essentially the same procedure as that described in Example 13. The pmr spectrum of the product was consistent with the assigned structure (chemical shift δ ppm): 0.9–1.4, 2xt, 6H; 1.4–1.7, d, 3H; 3.2–3.8, 2xt+3.44, s, 7H; 4.7–5.0, q, 1H, 6.7–7.3, m, 7H.

EXAMPLE 15

Preparation of Methyl 2-{4-[N-methyl-N-(5-nitro-2-thiazolyl)amino]phenoxy}propionate (52)

(a) 4-[N-methyl-N-(5-nitro-2-thiazolyl)amino]phenol

A mixture of 2-bromo-5-nitrothiazole (4.18 g), 4-(N-methylamino)phenol and water (50 ml) was heated under reflux for a period of 18 hours. The cooled solution was neutralised with aqueous potassium hydrogen carbonate and extracted with diethyl ether. The organic extract was dried over anhydrous magnesium sulfate and the solvent removed by distillation under reduced pressure to give 4-[N-methyl-N-(5-nitro-2-thiazolyl)amino]phenol (2.51 g) as an oil. The pmr spectrum of the compound was consistent with the assigned structure (CDCl$_3$; chemical shift δ ppm): 3.55, s, 3H; 5.85, br.s, 1H; 7.15, m, 4H; 8.20, s, 1H.

(b) Methyl 2-{4-[N-methyl-N-(5-nitro-2-thiazolyl)amino]phenoxy}propionate (52)

A mixture of 4-[N-methyl-N-(5-nitro-2-thiazolyl)amino]phenol (2.51 g), methyl 2-bromopropionate (1.67 g), anhydrous potassium carbonate (1.52 g) and methyl ethyl ketone (50 ml) was heated under reflux for a period of 18 hours. The mixture was cooled, extracted with dichloromethane and the organic extract was dried over anhydrous magnesium sulfate. The solvent was removed by distillation under reduced pressure to give a brown oil. The crude product was purified by chromatography over silica gel with dichloromethane elution to give the required product (1.2 g) as a colourless oil. The pmr spectrum of the product was consistent with the assigned structure (CDCl$_3$; chemical shift δ ppm): 1.65, d, 3H; 3.55, s, 3H; 3.85, s, 3H; 4.80, q, 1H; 7.20, m, 4H; 8.20, s, 1H.

EXAMPLE 16

A number of the compounds of the invention are oils and may be identified by pmr spectroscopy. For convenience, pmr spectroscopic data, or melting (boiling) points where appropriate, are recorded in Table 5 below.

TABLE 5

PART A

Proton Chemical Shift δ in ppm (CDCl$_3$)

| Compound No | Aryl Groups | A,B,D Groups | $R^1$ | $R^2$ | $R^3$ | W Group |
|---|---|---|---|---|---|---|
| 3 | 6.7–7.7,m,6H | 1.1–2.7, 2xt, 6H 3.9–4.6, 2xd, 4H | 3.6,s, 3H | 1.7,d, 3H | 4.9,q, 1H | see A, B, D |
| 5 | 6.8–7.7,m,7H | 2.4,s,3H | 3.6,s, 3H | 1.7,d, 3H | 4.8,q, 1H | 1.3,t, 3H 4.3,q, 2H |
| 6 | 6.8–7.5,m,6H | | 3.6,s, 3H | 1.7,d, 3H | 4.8,q, 1H | 1.3,t, 3H 4.3,q, 2H |
| 7 | 6.8–7.5,m,7H | | 3.6,s, 3H | 1.7,d, 3H | 4.8,q, 1H | 1.3,t, 3H 4.3,q, 2H |
| 8 | 6.8–7.5,m,6H | 2.6,s,3H | 3.6,s, 3H | 1.7,d, 3H | 4.8,q, 1H | 1.3,t, 3H 4.3,q, 2H |
| 15 | 6.8–7.5,m,5H 7.8–8.3,m,2H | | 3.5,s 3H | 1.7,d, 3H | 4.8,q, 1H | 3.8,s, 3H |
| 16 | 6.6–7.5,m,8H | | 3.4,s, 3H | 1.6,d, 3H | see W | 1.3,t, 3H 3.9–4.8,m, 3H |
| 17 | 6.4–7.7,m,7H | 3.1,s, 3H | 3.5,s, 3H | 1.6,d, 3H | 4.8,q, 1H | 1.2,t, 3H 4.3,q, 2H |

TABLE 5

PART B

| Compound No | Melting (Boiling) Point °C. | Compound No | Melting (Boiling) Point °C. |
|---|---|---|---|
| 1 | 128–130 | 43 | 139–140 |

TABLE 5-continued

PART B

| Compound No | Melting (Boiling) Point °C. | Compound No | Melting (Boiling) Point °C. |
|---|---|---|---|
| 4 | 86–88 | 44 | 86–88 |
| 9 | 104 | 45 | (190–200/0.03 mm) |
| 10 | 84–86 | | |
| 11 | 169–175 | 46 | 99.5–100.5 |
| 12 | 117–121 | | |
| 19 | 64.5–66.5 | 47 | 91–92 |
| 27 | (250/0.1 mm) | | |
| 32 | 159–162 | 49 | 72–74 |
| 33 | 95–96 | | |
| 34 | 111–113 | | |
| 35 | 64.5–71.5 | | |
| 38 | 92.5–93 | | |
| 41 | 69–72 | | |
| 42 | 119–122 | | |

EXAMPLE 17

Concentrated formulations of the compounds of the invention were prepared by:

(a) in the case of oils and waxy solids, dissolving the compound in toluene containing 7% v/v "Teric" N13 ("Teric" is a Trade Mark and "Teric" N13, a product of ethoxylation of nonylphenol, is available from ICI Australia Limited) and 3% v/v "Kemmat" SC15B ("Kemmat" is a Trade Mark and "Kemmat" SC15B is a formulation of calcium dodecylbenzene sulfonate); or (b) in the case of crystalline solids, adding 5 parts by weight of the compound and 1 part by weight of "Dyapol" PT ("Dyapol" is a Trade Mark and "Dyapol" PT is an anionic suspending agent) to 94 parts by weight of an aqueous solution containing 0.25% v/v of "Teric" N8 (a product of ethoxylation of nonylphenol) and ball-milling the mixture to produce a stable suspension.

The emulsifiable concentrates and suspensions were then diluted with water to give an aqueous composition of the required concentration suitable for use in the evaluation of the pre-emergence and post-emergence herbicidal activity of the compounds of the invention.

EXAMPLE 18

The pre-emergent herbicidal activity of the compounds of the invention formulated as described in Example 17 was assessed by the following procedure.

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glasshouse, lightly watered with an overhead spray to initiate germination and then sub-irrigated as required for optimum plant growth. After three weeks the boxes were removed from the glasshouse and the effect of the treatment was visually assessed. The results were presented in Table 6 where the damage to plants is rated on a scale of from 0 to 3 where 0 represents from 0 to 25% damage, 3 represents 75 to 99% kill and 3+ represents 100% kill.

A dash (—) means that no experiment was carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

TABLE 6

PRE-EMERGENCE HERBICIDAL ACTIVITY

| Compound No | Application Rate (kg/ha) | Wh | Ot | Rg | Jm | P | Ip | Ms | Sf |
|---|---|---|---|---|---|---|---|---|---|
| 1 | 5.0 | 1 | 0 | 3+ | 3 | 0 | 0 | 0 | 0 |
| 1 | 1.0 | 0 | 0 | 3 | 3 | 0 | 0 | 0 | 0 |
| 2 | 5.0 | 2 | 1 | 3+ | 3+ | 0 | 0 | 0 | 0 |
| 2 | 1.0 | 0 | 0 | 2 | 3+ | 0 | 0 | 0 | 0 |
| 2 | 0.5 | 0 | 0 | 3 | 3 | 0 | 0 | 0 | 0 |
| 5 | 5.0 | 0 | 0 | 1 | 2 | 0 | 0 | 0 | 0 |
| 5 | 1.5 | 0 | 0 | 1 | 1 | 0 | 0 | 0 | 0 |
| 6 | 5.0 | 0 | 0 | 1 | 3+ | 0 | 0 | 0 | 0 |
| 8 | 5.0 | 0 | 0 | 3+ | 2 | 0 | 0 | 0 | 0 |
| 9 | 5.0 | 2 | 2 | 3+ | 3+ | 0 | 0 | 0 | 0 |
| 9 | 1.0 | 0 | 0 | 3 | 3+ | 0 | 0 | 0 | 0 |
| 9 | 0.5 | 0 | 0 | 1 | 1 | 0 | 0 | 0 | 0 |

EXAMPLE 19

The post-emergent herbicidal activity of the compounds of the invention formulated as described in Example 17 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glasshouse, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glasshouse and sprayed with the required quantity of a composition of the invention. After spraying the boxes were returned to the glasshouse for further 3 weeks and the effects of treatment was visually assessed by comparison with the untreated controls. The results are presented in Table 7 where the damage to plants is rated on a scale of from 0 to 3 where 0 represents 0 to 25% damage, 3 represents 75 to 99% kill and 3+ represents 100% kill. A dash (—) means that no experiment was carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

TABLE 7

POST-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 1 | 5.0 | 2 | 0 | 3+ | 3+ | 0 | 0 | 0 | 0 |
| 1 | 1.0 | 0 | 0 | 3 | 3+ | 0 | 0 | 0 | 0 |
| 1 | 0.5 | 0 | 0 | 1 | 3+ | 0 | 0 | 0 | 0 |
| 2 | 5.0 | 2 | 3 | 3+ | 3+ | 0 | 0 | 0 | 0 |
| 2 | 0.5 | 3 | 2 | 3 | 3+ | 0 | 0 | 0 | 0 |
| 5 | 5.0 | 3+ | 0 | 3+ | 3+ | 0 | 0 | 0 | 0 |
| 5 | 1.5 | 2 | 0 | 3 | 3+ | 0 | 0 | 0 | 0 |
| 6 | 5.0 | 3 | 3 | 3 | 3 | 0 | 0 | 0 | 0 |
| 8 | 5.0 | 0 | 0 | 2 | 2 | 0 | 0 | 0 | 0 |
| 9 | 5.0 | 3+ | 3+ | 3+ | 3+ | 0 | 0 | 0 | 0 |
| 9 | 1.0 | 3+ | 3+ | 3+ | 3+ | 0 | 0 | 0 | 0 |
| 9 | 0.5 | 3+ | 3+ | 3+ | 3+ | 0 | 0 | 0 | 0 |
| 50 | 10.0 | 0 | 0 | 0 | 1 | 0 | 2 | 3+ | 0 |

EXAMPLE 20

This Example illustrates the herbicidal properties of the compounds used in the process of the invention. Each compound was formulated for test by mixing an appropriate amount of it with 5 ml of an emulsion prepared by diluting 160 ml of a solution containing 21.8 grams per liter of Span 80 and 78.2 grams per liter of Tween 20 in methyl cyclohexanone to 500 ml with water. Span 80 is a Trade Mark for a surface-active agent comprising sorbitan monolaurate. Tween 20 is a Trade Mark for a surface-active agent comprising a condensate of twenty molar proportions of ethylene oxide with sorbitan mono-oleate. The mixture of the compound and the emulsion was shaken with glass beads and diluted to 40 ml with water.

The spray compositions so prepared were sprayed on to young pot plants (post-emergence test) of the species named in Table 8 below, at a rate equivalent to 1000 liters per hectare. Damage to plants was assessed 14 days after spraying by comparison with untreated plants, on a scale of 0 to 5 where 0 is 0 to 20% kill and 5 represents 100% kill. In a test for pre-emergence herbicidal activity, seeds of the test species were placed on the surface of fibre trays of soil and were sprayed with the compositions at the rate of 1000 liters per hectare. The seeds were then covered with further soil. Three weeks after spraying, the seedlings in the sprayed fibre trays were compared with the seedlings in unsprayed control trays, the damage being assessed on the same scale of 0 to 5. The results are given in Table 8 below. A dash (−) means that no test was made.

The names of the test plants were as follows:

| | |
|---|---|
| Sb | Sugar beet |
| Rp | Rape |
| Ct | Cotton |
| Sy | Soy bean |
| Mz | Maize |
| Mw | Winter wheat |
| Rc | Rice |
| Sn | *Senecio vulgaris* |
| Ip | *Ipomea purpurea* |
| Am | *Amaranthus retroflexus* |
| Pi | *Polygonum aviculare* |
| Ca | *Chenopodium album* |
| Po | *Portulaca oleracea* |
| Xa | *Xanthium pensylvanicum* |
| Ab | *Abutilon theophrasti* |
| Cv | *Convolvulus arvensis* |
| Ot | Cultivated oats and wild oats (*Avena fatua*) Wild oats are used in the post-emergence test and cultivated oats in the pre-emergence test |
| Dg | *Digitaria sanguinalis* |
| Pu | *Poa annua* |
| St | *Setaria viridis* |
| Ec | *Echinochloa crus-galli* |
| Sh | *Sorghum halepense* |
| Ag | *Agropyron repens* |
| Cn | *Cyperus rotundus* |

TABLE 8

PART A

| Compound No | APPLICATION Method | Rate (kg/ha) | Sb | Rp | Ct | Sy | Mz | Ww | Rc | Sn | Ip | Am | Pi | Ca |
|---|---|---|---|---|---|---|---|---|---|---|---|---|---|---|
| 2 | PRE | 0.2 | 2 | 0 | 0 | 0 | 0 | 0 | 0 | 0 | 0 | 2 | 0 | — |
| 2 | POST | 0.2 | 0 | 0 | 0 | 0 | 4 | 4 | 2 | 0 | 0 | 0 | 0 | 0 |
| 2 | POST | 0.05 | 0 | 0 | 0 | 0 | 1 | 4 | 0 | 0 | 0 | 0 | 0 | 0 |
| 5 | PRE | 2.0 | 0 | 0 | 0 | 0 | 0 | 2 | 1 | 0 | 0 | 0 | 0 | 0 |
| 5 | POST | 2.0 | 0 | 0 | 0 | 0 | 5 | 3 | 2 | 0 | 0 | 0 | 0 | 1 |
| 6 | PRE | 2.0 | 0 | 0 | 0 | 0 | 0 | 1 | 1 | 0 | 0 | 1 | 0 | 0 |
| 6 | POST | 2.0 | 0 | 0 | 0 | 0 | 4 | 2 | 0 | 1 | 0 | 1 | 0 | 0 |
| 7 | PRE | 2.0 | 1 | 0 | 0 | 0 | 0 | 0 | 0 | 0 | 0 | 0 | 0 | 0 |
| 7 | POST | 2.0 | 0 | 0 | 0 | 0 | 2 | 0 | 0 | 1 | 0 | 2 | 0 | 1 |
| 9 | PRE | 2.0 | 0 | 0 | 0 | 0 | 5 | 5 | 3 | 0 | 0 | 1 | 0 | 3 |
| 9 | POST | 2.0 | 1 | 0 | 0 | 0 | 4 | 4 | 2 | 1 | 1 | — | 0 | 1 |
| 10 | PRE | 2.0 | 0 | 0 | 0 | 0 | 5 | 5 | 4 | 0 | 2 | 0 | 0 | 1 |
| 10 | PRE | 0.5 | 0 | 0 | 0 | 0 | 3 | 4 | 3 | 0 | 1 | 1 | 0 | 0 |
| 10 | PRE | 0.2 | 0 | 0 | 0 | 0 | 3 | 2 | 2 | 0 | 0 | 0 | 0 | 0 |
| 10 | POST | 2.0 | 0 | 0 | 0 | 2 | 5 | 4 | 4 | 0 | 0 | 2 | 0 | 0 |
| 10 | POST | 0.5 | 0 | 0 | 0 | 2 | 4 | 4 | 2 | 0 | 0 | 0 | 0 | 0 |
| 10 | POST | 0.2 | 0 | 0 | 0 | 0 | 4 | 3 | 0 | 0 | 0 | — | 0 | — |
| 11 | PRE | 2.0 | 0 | 0 | 0 | 0 | 4 | 4 | 4 | 0 | 0 | 3 | 1 | 2 |
| 11 | PRE | 0.5 | 0 | 1 | 0 | 0 | 3 | 3 | 2 | — | 0 | 2 | 0 | 1 |
| 11 | POST | 2.0 | 0 | 2 | 0 | 2 | 5 | 4 | 4 | 0 | 0 | 0 | 1 | — |
| 11 | POST | 0.5 | 0 | 0 | 0 | 0 | 4 | 4 | 3 | 0 | 0 | 1 | 0 | — |
| 12 | PRE | 2.0 | 0 | 0 | 0 | 0 | 1 | 0 | 2 | 1 | 0 | 0 | 0 | 0 |
| 12 | POST | 2.0 | 0 | 0 | 0 | 0 | 2 | 0 | 0 | 0 | 0 | 0 | 0 | 0 |
| 13 | PRE | 2.0 | 0 | 0 | 0 | 0 | 0 | 0 | 0 | 1 | 0 | 1 | 0 | — |
| 14 | PRE | 0.5 | 0 | 0 | 0 | 0 | 0 | 0 | 0 | 3 | 0 | 2 | 0 | — |
| 15 | PRE | 1.5 | 0 | 0 | 0 | 0 | 0 | 0 | 0 | 2 | 0 | 2 | 0 | — |
| 16 | PRE | 2.0 | 0 | 0 | 0 | 0 | 0 | 0 | 0 | 2 | 0 | 0 | 1 | — |
| 17 | POST | 2.0 | 3 | 0 | 0 | 0 | 0 | 0 | 0 | — | 0 | 2 | 0 | 1 |
| 18 | PRE | 5.0 | 0 | 0 | 0 | 0 | 2 | 4 | 5 | 5 | 0 | 0 | 0 | 0 |

TABLE 8-continued
PART A

| Compound No | APPLICATION Method | Rate (kg/ha) | Sb | Rp | Ct | Sy | Mz | Ww | Rc | Sn | Ip | Am | Pi | Ca |
|---|---|---|---|---|---|---|---|---|---|---|---|---|---|---|
| 18 | PRE | 1.0 | 0 | 0 | 0 | 0 | 4 | 5 | 5 | 0 | 0 | 0 | 0 | 0 |
| 18 | PRE | 0.2 | 0 | 0 | 0 | 0 | 3 | 4 | 5 | 0 | 0 | 0 | 0 | 0 |
| 18 | PRE | 0.1 | 0 | 0 | 0 | 0 | 0 | 2 | 2 | 0 | 0 | 0 | — | 0 |
| 18 | PRE | 0.05 | 0 | 0 | 0 | 1 | 1 | 3 | 4 | 0 | 0 | 1 | 0 | 0 |
| 18 | POST | 5.0 | 1 | 2 | 1 | 3 | 5 | 4 | 4 | 1 | 0 | 3 | 3 | 1 |
| 18 | POST | 1.0 | 0 | 0 | 0 | 0 | 5 | 4 | 4 | 1 | 0 | 0 | 1 | 0 |
| 18 | POST | 0.2 | 0 | 0 | 0 | 0 | 5 | 4 | 2 | 0 | 0 | 0 | 0 | 0 |
| 18 | POST | 0.1 | 0 | 0 | 0 | 0 | — | 4 | 4 | 0 | 0 | 0 | 0 | 3 |
| 18 | POST | 0.05 | 0 | — | 0 | 0 | 5 | 4 | 3 | 0 | 0 | 0 | 0 | 0 |
| 29 | PRE | 5.0 | 0 | 0 | 2 | 0 | 0 | 0 | 0 | 0 | 0 | 0 | 0 | — |
| 29 | POST | 5.0 | 1 | 0 | 0 | 0 | 0 | 0 | 0 | 3 | 0 | 4 | 3 | 3 |
| 30 | PRE | 5.0 | 1 | 0 | 0 | 1 | 4 | 4 | 5 | 3 | 2 | 0 | 0 | — |
| 30 | POST | 5.0 | 1 | 0 | 0 | 3 | 5 | 4 | 4 | 0 | 0 | 3 | 3 | 3 |
| 31 | PRE | 0.04 | 1 | 0 | 0 | 1 | 0 | 0 | 0 | 0 | 1 | — | — | — |
| 31 | POST | 0.04 | 0 | 0 | 0 | 0 | 5 | 4 | 2 | 2 | 0 | 0 | — | 0 |
| 32 | PRE | 5.0 | 1 | 1 | 2 | 1 | 0 | 0 | 0 | 0 | 0 | 0 | 0 | 0 |
| 32 | POST | 5.0 | 1 | 1 | 1 | 1 | 4 | 0 | 0 | 2 | 0 | 2 | 2 | 2 |
| 34 | PRE | 2.0 | 1 | 0 | — | 0 | 1 | 4 | 3 | 0 | 0 | 0 | 0 | 0 |
| 34 | PRE | 0.1 | 0 | 2 | 0 | 0 | 0 | 0 | 0 | 0 | 0 | 0 | — | 0 |
| 34 | POST | 2.0 | 0 | 1 | 0 | 1 | 4 | 4 | 2 | 0 | 0 | — | 1 | — |
| 34 | POST | 0.1 | 1 | 0 | 0 | 0 | — | 1 | 0 | 1 | 0 | 0 | 0 | 4 |
| 36 | PRE | 0.04 | 1 | 0 | 0 | 0 | 0 | 0 | 0 | 0 | 0 | 0 | — | — |
| 36 | POST | 0.04 | 0 | 0 | 0 | 0 | 4 | 3 | 0 | 2 | 0 | 3 | — | 3 |
| 37 | PRE | 2.0 | 0 | 0 | 0 | 0 | 4 | 4 | 5 | — | 0 | 1 | 0 | 0 |
| 37 | PRE | 0.5 | 0 | 0 | 0 | 0 | 0 | 3 | 2 | 0 | 1 | — | 0 | 0 |
| 37 | POST | 2.0 | 0 | 1 | 3 | 2 | 4 | 4 | 2 | 3 | 0 | — | 3 | — |
| 37 | POST | 0.5 | 0 | 0 | 2 | 0 | 4 | 3 | 1 | 2 | 0 | — | 0 | — |
| 38 | PRE | 0.1 | 0 | 0 | 1 | 0 | 2 | 0 | 0 | 0 | 0 | 0 | — | 0 |
| 38 | POST | 0.1 | 0 | 1 | 2 | 0 | 5 | 4 | 1 | 4 | 1 | 3 | 0 | 0 |
| 39 | PRE | 2.0 | 0 | 0 | 0 | 0 | 5 | 3 | 3 | 0 | 0 | 0 | 0 | 0 |
| 39 | PRE | 0.5 | 0 | 0 | 0 | 0 | 2 | 1 | 0 | 0 | 0 | 0 | — | 0 |
| 39 | POST | 2.0 | 0 | 1 | 0 | 2 | 5 | 3 | 3 | 0 | 0 | 2 | 0 | 2 |
| 39 | POST | 0.5 | 0 | 0 | 1 | 0 | 4 | 3 | 3 | 0 | 0 | 3 | 0 | 0 |
| 41 | PRE | 0.2 | 0 | 0 | 0 | 0 | 2 | 2 | 0 | 0 | 0 | 0 | 0 | — |
| 41 | POST | 0.2 | 0 | 0 | 0 | 0 | 5 | 3 | 0 | 0 | 0 | 0 | 0 | 1 |

TABLE 8
PART B

| Compound No | APPLICATION Method | Rate (kg/ha) | Po | Xa | Ab | Cv | Ot | Dg | Pu | St | Ec | Sh | Ag | Cn |
|---|---|---|---|---|---|---|---|---|---|---|---|---|---|---|
| 2 | PRE | 0.2 | 0 | 0 | 0 | — | 0 | 4 | 0 | 0 | 0 | 0 | 1 | 0 |
| 2 | POST | 0.2 | 0 | 0 | 1 | 0 | 4 | 1 | 0 | 4 | 5 | 5 | 3 | 0 |
| 2 | POST | 0.05 | 0 | 0 | 0 | 0 | 2 | 1 | 0 | 4 | 3 | 5 | 2 | 0 |
| 5 | PRE | 2.0 | 2 | 0 | 1 | — | 1 | 2 | 0 | 4 | 3 | 3 | 0 | 0 |
| 5 | POST | 2.0 | — | 0 | 0 | 0 | 0 | 1 | 0 | 5 | 5 | 3 | 3 | — |
| 6 | PRE | 2.0 | 0 | 0 | 1 | — | 1 | 0 | 0 | 1 | 1 | 4 | 0 | 0 |
| 6 | POST | 2.0 | — | 0 | 0 | 0 | 2 | 3 | 0 | 4 | 4 | 3 | 0 | — |
| 7 | PRE | 2.0 | 0 | 0 | 1 | — | 0 | 0 | 0 | 0 | 2 | 0 | 0 | 0 |
| 7 | POST | 2.0 | — | 0 | 0 | 1 | 0 | 0 | 0 | 2 | 2 | 0 | 0 | — |
| 9 | PRE | 2.0 | 3 | 0 | 0 | — | 4 | 5 | 2 | 4 | 5 | 4 | 0 | 0 |
| 9 | POST | 2.0 | 2 | 0 | 1 | 0 | 5 | 5 | 2 | 5 | 5 | 5 | 5 | 0 |
| 10 | PRE | 2.0 | 0 | 0 | 0 | — | 2 | 4 | 3 | 4 | 5 | 2 | 2 | 0 |
| 10 | PRE | 0.5 | 0 | 0 | 0 | — | 1 | 3 | 1 | 4 | 4 | 2 | 0 | 0 |
| 10 | PRE | 0.2 | 0 | 0 | 0 | — | 0 | 3 | 0 | 0 | 3 | 2 | 0 | 0 |
| 10 | POST | 2.0 | 0 | 0 | 0 | 0 | 0 | 2 | 0 | 4 | 5 | 4 | 4 | 1 |
| 10 | POST | 0.5 | 0 | 0 | 0 | 0 | 0 | 0 | 0 | 5 | 4 | 2 | 2 | 0 |
| 10 | POST | 0.2 | 0 | 0 | 0 | 0 | 0 | 0 | 0 | 0 | 5 | 4 | 3 | 0 |
| 11 | PRE | 2.0 | 0 | 0 | 0 | — | 3 | 4 | 2 | 4 | 5 | 4 | 4 | 0 |
| 11 | PRE | 0.5 | 1 | 0 | 0 | — | 2 | 4 | 0 | 2 | 4 | 3 | 2 | 0 |
| 11 | POST | 2.0 | 0 | 0 | 0 | 0 | 1 | 2 | 0 | 3 | 5 | 4 | 3 | 0 |
| 11 | POST | 0.5 | 0 | 0 | 0 | 0 | 0 | 0 | 0 | 1 | 5 | 1 | 1 | 0 |
| 12 | PRE | 2.0 | 0 | 0 | 0 | — | 2 | 1 | 0 | 0 | 2 | 0 | 0 | 0 |
| 12 | POST | 2.0 | 0 | 0 | 0 | 0 | 0 | 0 | 0 | 2 | 0 | 1 | 0 | 0 |
| 13 | PRE | 2.0 | 2 | 0 | 2 | — | 0 | 0 | 0 | 0 | 0 | 0 | 0 | 0 |
| 14 | PRE | 0.5 | 0 | 0 | 0 | — | 0 | 0 | 0 | 0 | 2 | 0 | 0 | 0 |
| 15 | PRE | 1.5 | 1 | 1 | 1 | — | 0 | 2 | 0 | 0 | 0 | 1 | 0 | 1 |
| 16 | PRE | 2.0 | 0 | 2 | 0 | — | 0 | 0 | 0 | 0 | 0 | 0 | 0 | 0 |
| 17 | POST | 2.0 | 0 | 0 | 0 | 0 | 0 | 0 | 0 | 2 | 0 | 1 | 0 | 0 |
| 18 | PRE | 5.0 | 0 | 0 | 0 | — | 4 | 5 | 5 | 5 | 5 | 5 | 1 | 0 |
| 18 | PRE | 1.0 | 0 | 0 | 0 | 0 | 4 | 5 | 5 | 5 | 5 | 4 | 0 | 0 |
| 18 | PRE | 0.2 | 0 | 0 | 0 | 0 | 2 | 4 | 4 | 4 | 2 | 2 | 0 | 0 |
| 18 | PRE | 0.1 | 0 | 0 | 0 | — | 1 | 3 | 0 | 4 | 2 | — | 0 | 0 |
| 18 | PRE | 0.05 | 0 | 0 | 0 | — | 0 | 1 | 0 | 4 | 3 | 0 | 0 | 0 |

TABLE 8-continued

PART B

| Compound No | APPLICATION Method | Rate (kg/ha) | Po | Xa | Ab | Cv | Ot | Dg | Pu | St | Ec | Sh | Ag | Cn |
|---|---|---|---|---|---|---|---|---|---|---|---|---|---|---|
| 18 | POST | 5.0 | 2 | 3 | 0 | 0 | 5 | 5 | 4 | 5 | 5 | 5 | 4 | 0 |
| 18 | POST | 1.0 | 0 | 0 | 0 | 0 | 5 | 5 | 4 | 5 | 5 | 5 | 4 | 0 |
| 18 | POST | 0.2 | 0 | 0 | 0 | 0 | 4 | 4 | 2 | 5 | 4 | 5 | 3 | 0 |
| 18 | POST | 0.1 | 0 | 0 | 0 | 0 | 4 | 5 | 0 | 5 | 4 | 5 | 2 | 0 |
| 18 | POST | 0.05 | 0 | 0 | 0 | 0 | 4 | 4 | 0 | 4 | 3 | — | 2 | 0 |
| 29 | PRE | 5.0 | 0 | 0 | 0 | — | 0 | 2 | 0 | 0 | 1 | 0 | 2 | 0 |
| 29 | POST | 5.0 | 1 | 1 | 0 | 0 | 0 | 0 | 0 | 0 | 0 | 1 | 0 | 0 |
| 30 | PRE | 5.0 | 0 | 0 | 0 | — | 2 | 4 | 0 | 4 | 5 | 4 | 5 | 0 |
| 30 | POST | 5.0 | 1 | 0 | 0 | 0 | 0 | 0 | 0 | 1 | 4 | 4 | 4 | 0 |
| 31 | PRE | 0.04 | 0 | 0 | 0 | — | 0 | 0 | 0 | 0 | 0 | 0 | 0 | 0 |
| 31 | POST | 0.04 | 1 | 0 | 2 | 0 | 2 | 2 | 0 | 5 | 1 | 4 | 0 | 0 |
| 32 | PRE | 5.0 | 0 | 0 | 0 | — | 0 | 0 | 0 | 0 | 0 | — | 0 | — |
| 32 | POST | 5.0 | 0 | 2 | 0 | 0 | 0 | 0 | 0 | 0 | 0 | 0 | 0 | 0 |
| 34 | PRE | 2.0 | 0 | 0 | 2 | — | 2 | 4 | 0 | 4 | 3 | 4 | 0 | 0 |
| 34 | PRE | 0.1 | 0 | 0 | 0 | — | 0 | 1 | 0 | 0 | 0 | — | 1 | — |
| 34 | POST | 2.0 | 0 | 0 | 0 | 0 | 4 | 5 | 0 | 4 | 5 | 5 | 2 | 0 |
| 34 | POST | 0.1 | 2 | 0 | 0 | 2 | 0 | 4 | 0 | 4 | 4 | 4 | 0 | 0 |
| 36 | PRE | 0.04 | 0 | 1 | 0 | — | 0 | 0 | 1 | 0 | 0 | 0 | 0 | 0 |
| 36 | POST | 0.04 | 3 | 2 | 1 | 2 | 3 | 1 | 0 | 4 | 3 | 4 | 0 | 0 |
| 37 | PRE | 2.0 | 2 | 0 | 0 | — | 3 | 5 | 0 | 5 | 5 | 5 | 4 | 5 |
| 37 | PRE | 0.5 | 0 | 0 | 0 | — | 1 | 3 | 0 | 4 | 1 | 3 | 0 | 0 |
| 37 | POST | 2.0 | 1 | 0 | 1 | 0 | 4 | 4 | 3 | 5 | 5 | 5 | 3 | 1 |
| 37 | POST | 0.5 | 1 | 0 | 0 | 0 | 4 | 4 | 0 | 4 | 4 | 4 | 3 | 0 |
| 38 | PRE | 0.1 | 0 | 0 | 0 | — | 2 | 0 | 0 | 0 | 0 | — | 0 | 0 |
| 38 | POST | 0.1 | 0 | 1 | 0 | 0 | 3 | 5 | 0 | 4 | 5 | 5 | 1 | 0 |
| 39 | PRE | 2.0 | 0 | 0 | 0 | — | 2 | 5 | 0 | 5 | 5 | 0 | 4 | 0 |
| 39 | PRE | 0.5 | 0 | 0 | 0 | — | 0 | 2 | 0 | 0 | 0 | 0 | 0 | 0 |
| 39 | POST | 2.0 | 0 | 0 | 0 | 0 | 4 | 4 | 0 | 4 | 4 | 5 | 2 | 2 |
| 39 | POST | 0.5 | 0 | 0 | 0 | 0 | 4 | 4 | 0 | 4 | 4 | 4 | 2 | 0 |
| 41 | PRE | 0.2 | 1 | 0 | 0 | — | 1 | 0 | 0 | 4 | 2 | 2 | 0 | 0 |
| 41 | POST | 0.2 | 0 | 0 | 0 | 0 | 1 | 0 | 0 | 4 | 4 | 4 | 2 | 0 |

We claim:

1. A compound

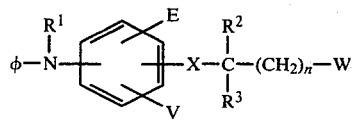

or a salt thereof wherein:

φ is the group

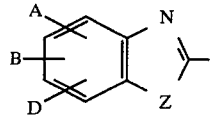

in which Z is chosen from O, S, NH and N-C$_1$ to C$_6$ alkyl;

A, B and D are independently chosen from the group consisting of hydrogen, halogen, nitro, C$_1$ to C$_6$ alkyl, C$_1$ to C$_6$ haloalkyl and C$_1$ to C$_6$ alkoxy;

E and V are independently chosen from the group consisting of hydrogen, halogen and nitro;

R$^1$ is chosen from the group consisting of hydrogen, C$_1$ to C$_6$ alkyl, C$_2$ to C$_6$ alkenyl, C$_2$ to C$_6$ alkynyl, C$_2$ to C$_6$ alkanoyl and benzyl;

R$^2$ and R$^3$ are independently chosen from hydrogen and C$_1$ to C$_6$ alkyl;

W is

wherein: G is chosen from the group consisting of hydroxy, C$_1$ to C$_{10}$ alkoxy, C$_2$ to C$_{10}$ alkenyloxy, C$_2$ to C$_{10}$ alkynyloxy, C$_3$ to C$_7$ cycloalkoxy, benzyloxy, C$_1$ to C$_{10}$ alkylthio, amino, N-(C$_1$ to C$_6$ alkyl)amino, N,N-di(C$_1$ to C$_6$ alkyl)amino, C$_1$ to C$_{10}$ alkoxy substituted with a substituent chosen from amino, ammonio, N-(C$_1$ to C$_6$ alkyl)amino, N,N-di(C$_1$ to C$_6$ alkyl)amino and N,N,N-tri(C$_1$ to C$_6$ alkyl)ammonio, and the group OM wherein M is an alkali metal or alkaline earth metal ion;

X is oxygen; and n is 0 or 2.

2. A compound according to claim 1 of the formula

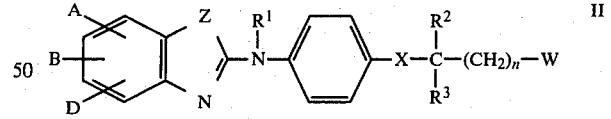

3. A compound according to claim 1 wherein:

A, B and D are independently chosen from the group consisting of hydrogen, halogen, nitro, C$_1$ to C$_6$ alkyl and C$_1$ to C$_6$ haloalkyl;

R$^1$ is chosen from the group consisting of hydrogen, C$_1$ to C$_6$ alkyl, C$_2$ to C$_6$ alkenyl, C$_2$ to C$_6$ alkynyl and benzyl;

R$^2$ is chosen from hydrogen and C$_1$ to C$_6$ alkyl; R$^3$, E and V are hydrogen;

X is oxygen;

W is the group

4. A compound according to claim 1 wherein:
φ is the group

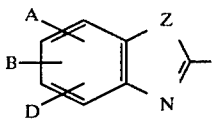

wherein
Z is oxygen or sulfur;
A is a chloro, bromo or trifluoromethyl substituent in the 5- or 6-position of the ring system;
$R^1$ is chosen from hydrogen and $C_1$ to $C_6$ alkyl;
$R^2$ is methyl;
$R^3$, B, D, E and V are hydrogen;
X is oxygen;
W is the group

wherein G is chosen from hydroxy, cyclohexyloxy and $C_1$ to $C_8$ alkoxy; and
n is 0.

5. A compound according to claim 1 wherein:
φ is the group

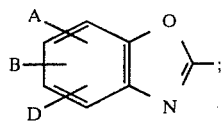

A is a chloro or bromo substituent in the 5-position of the ring system;
$R^1$ and $R^2$ are both methyl;
$R^3$, B, D, E and V are all hydrogen;
X is oxygen;
W is the group

wherein G is chosen from $C_1$ to $C_6$ alkoxy; and
n is 0.

6. A compound according to claim 1 chosen from the group consisting of:
methyl 2-{4-[N-methyl-N-(5-chloro-2-benzothiazolyl)amino]phenoxy}propionate;
ethyl 2-{4-[N-methyl-N-(5-chloro-2-benzoxazolyl)amino]phenoxy}propionate;
ethyl 2-{4-[N-methyl-N-(5-bromo-2-benzoxazolyl)amino]phenoxy}propionate;
ethyl 2-{4-[N-methyl-N-(5-trifluoromethyl-2-benzoxazolyl)amino]phenoxy}propionate; and
ethyl 2-{4-[N-methyl-N-(6-chloro-2-benzoxazolyl)amino]phenoxy}propionate.

* * * * * wherein G is chosen from hydroxy, $C_1$ to $C_6$ alkoxy, $C_2$ to $C_6$ alkenyloxy and $C_2$ to $C_6$ alkynyloxy; and
n is 0.